United States Patent
Chiang et al.

(10) Patent No.: US 9,823,212 B2
(45) Date of Patent: *Nov. 21, 2017

(54) SETTING METHOD FOR CONDUCTIVE OBJECT OF ELECTROCHEMICAL TEST STRIP

(71) Applicant: KUANG HONG PRECISION CO., LTD., Taoyuan (TW)

(72) Inventors: Cheng-Feng Chiang, Taoyuan (TW); Jung-Chuan Chiang, Taoyuan (TW); Wen-Te Chiang, Taoyuan (TW); Chien-Ying Chiang, Taoyuan (TW); Chien-Yi Chiang, Taoyuan (TW)

(73) Assignee: KUANG HONG PRECISION CO., LTD., Taoyuan (TW)

( * ) Notice: Subject to any disclaimer, the term of this patent is extended or adjusted under 35 U.S.C. 154(b) by 256 days.

This patent is subject to a terminal disclaimer.

(21) Appl. No.: 14/753,068

(22) Filed: Jun. 29, 2015

(65) Prior Publication Data

US 2016/0018352 A1    Jan. 21, 2016

(30) Foreign Application Priority Data

Jul. 17, 2014   (CN) .......................... 2014 1 0341613

(51) Int. Cl.
| | | |
|---|---|---|
| *H01R 43/16* | (2006.01) | |
| *G01N 27/327* | (2006.01) | |
| *B29C 45/14* | (2006.01) | |
| *B29K 705/00* | (2006.01) | |

(52) U.S. Cl.
CPC .... *G01N 27/3272* (2013.01); *B29C 45/14639* (2013.01); *B29K 2705/00* (2013.01)

(58) Field of Classification Search
CPC .............. B29C 45/14639; B21D 28/02; B29K 2705/00; G01N 27/307; G01N 27/3272; C23C 18/1641
See application file for complete search history.

(56) References Cited

U.S. PATENT DOCUMENTS

| | | | | |
|---|---|---|---|---|
| 5,997,817 A | * | 12/1999 | Crismore | C12Q 1/001 204/403.1 |
| 7,387,714 B2 | * | 6/2008 | Gundel | G01N 27/3272 204/400 |
| 2004/0108206 A1 | * | 6/2004 | Bhullar | C12Q 1/004 204/403.01 |
| 2004/0251132 A1 | * | 12/2004 | Leach | C12Q 1/006 204/403.01 |
| 2006/0266645 A1 | * | 11/2006 | Chen | G01N 27/3272 204/403.01 |
| 2007/0110615 A1 | * | 5/2007 | Neel | G01N 33/48771 422/400 |

(Continued)

FOREIGN PATENT DOCUMENTS

| | | |
|---|---|---|
| CN | 203811568 U | 9/2014 |
| TW | I245119 B | 12/2005 |

*Primary Examiner* — Paul D Kim

(57) ABSTRACT

The present invention relates a setting method for a conductive object of electrochemical test strip. In the embodiment, this manufacturing process is not complex, convenient, and has well precision, such that the cost of manufacturing an electrochemical test strip is reduced effectively, and the disadvantage of past manufacturing process is improved. The present invention is highly applied and convenient, so that wide application can be expected in the future.

4 Claims, 13 Drawing Sheets

(56) References Cited

U.S. PATENT DOCUMENTS

| | | | | |
|---|---|---|---|---|
| 2015/0276670 A1* | 10/2015 | Wu | ............... | G01N 27/3273 205/775 |
| 2015/0338366 A1* | 11/2015 | Chiang | ............... | C23C 18/1641 205/164 |
| 2016/0377570 A1* | 12/2016 | Chiang | ............... | G01N 27/3272 156/245 |

* cited by examiner

SETTING METHOD FOR CONDUCTIVE OBJECT OF ELECTROCHEMICAL TEST STRIP

CROSS-REFERENCE TO RELATED APPLICATION

This application claims the benefit of Chinese Patent Application No. 201410341613.1, filed on Jul. 17, 2014, in the State Intellectual Property Office of the P.R.C, the invention of which is incorporated herein in its entirety by reference.

BACKGROUND OF THE INVENTION

1. Field of the Invention

The present invention relates to a setting method for a conductive object of an electrochemical test strip. In particular, it relates to a manufacturing method of disposable test strip.

2. Description of the Related Art

As the improvement of medical science and manufacturing process of the related equipment, a disposable test strip which has a metal electrode and is adapted for inspecting liquid sample, such as blood, to further inspect concentration of the blood sugar, uric acid, cholesterol in the blood or concentration of the heavy metal and insecticide in sewage, is well developed and widely applied, and becomes an importance testing tool.

The electrochemical testing principle is widely applied to test various liquid samples. However, as disclosed in Taiwan issue no. 1245119, which is titled as "structure of electrochemical test strip and manufacturing process thereof", the main body has a through hole, and at least one physical electrode is embedded into the main body and fixed in the through hole to conduct signal, so that the structure of combining multiple layers can be avoided, and the testing function can be improved.

However, the manufacturing process for product is not easy actually, and has the problem of complex and requiring multiple processes to finish the product. Moreover, these processes are necessary to set electrodes on an inspection portion and only can be finished by the apparatuses with high precision. It causes the increasing of the manufacturing cost and is hard to lower the price. Therefore, it is not easy to widely apply.

What is need is a setting method for a conductive object of an electrochemical test strip to improve the conventional technology, solve above-mentioned problems, and enhance application widely for industry.

SUMMARY OF THE INVENTION

The present invention illustrates a setting method for a conductive object of an electrochemical test strip to solve the above-mentioned problems.

To achieve above-mentioned objective, the present invention provides a setting method for a conductive object of an electrochemical test strip comprising: A. molding a metal conductive rack step, to mold the metal conductive rack on a conductive metal substrate by a metal processing method, the metal conductive rack including a holder connected to a plurality of conductive objects; wherein each the conductive object respectively comprises an information reception end having an external contact surface, and each the conductive object further comprises an information outputting end having a transmission contact surface; B. embedded injection of a conductive inspection body step, to inject molding the inspection body of a polymer plastic material from the plurality of conductive objects on the metal conductive rack, and the external contact surface of the information reception end and the transmission contact surface of the information outputting end exposing from the inspection body; wherein a side of the inspection body comprises an inspection portion, and each the external contact surface of the information reception end exposes from the surface of inspection portion; and C. taking out the inspection body step, to get the inspection body from the holder of the metal conductive rack.

Preferably, the transmission contact surface of the information outputting end is disposed on an opposite side of the external contact surface and keeps the external contact surface at a distance, and the transmission contact surface and the external contact surface are respectively disposed on both sides of the inspection body.

Alternatively, the transmission contact surface of the information outputting end is disposed on an identical side of the external contact side Preferably, a surface protection layer further covers on the surface of the metal conductive rack after molding.

Preferably, a strengthened signal metal layer is formed on the external contact surface of the information contact end and the transmission contact surface of the information outputting end.

According to the setting method for the conductive object of the electrochemical test strip, the manufacturing process of the electrochemical test strip is not complex and has more precision and convenience, so the manufacturing cost can be reduced efficiently. Therefore, the present invention can be widely applied.

Many of the attendant features and advantages of the present invention will becomes better understood with reference to the following detailed description considered in connection with the accompanying drawings.

BRIEF DESCRIPTION OF THE DRAWINGS

The detailed structure, operating principle and effects of the present invention will now be described in more details hereinafter with reference to the accompanying drawings that show various embodiments of the present invention as follows.

DETAILED DESCRIPTION OF THE PREFERRED EMBODIMENTS

Figure 1:
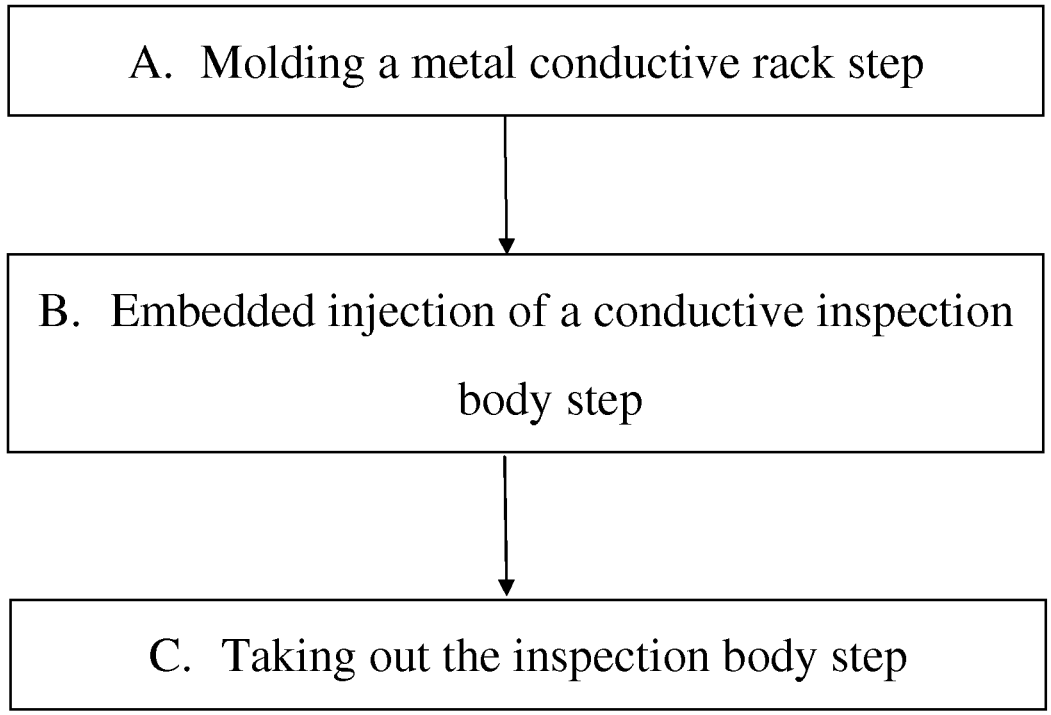
FIG. 1 is a flow diagram of the setting method for the conductive object of the electrochemical test strip in the present invention.

Reference will now be made in detail to the exemplary embodiments of the present invention, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this invention will be thorough and complete, and will fully convey the inventive concept to those skilled in the art. The relative proportions and ratios of elements in the drawings may be exaggerated or diminished in size for the sake of clarity and convenience in the drawings, and such arbitrary proportions are only illustrative and not limiting in any way. The same reference numbers are used in the drawings and the description to refer to the same or like parts.

It will be understood that, although the terms 'first', 'second', 'third', etc., may be used herein to describe various elements, these elements should not be limited by these terms. The terms are used only for the purpose of distinguishing one component from another component. Thus, a first element discussed below could be termed a second element without departing from the teachings of embodiments. As used herein, the term "or" includes any and all combinations of one or more of the associated listed items.

For convenience, certain terms employed in the specification, examples and appended claims are collected here. Unless defined otherwise, all technical and scientific terms used herein have the same meaning as commonly understood by one of the ordinary skill in the art to which this invention belongs.

Please refer to FIG. 1, the present invention provides a setting method for a conductive object of an electrochemical test strip comprising; wherein the method preferably comprises: A. molding a metal conductive rack step; B. embedded injection of a conductive inspection body step; and C. taking out the inspection body step.

Figure 2:
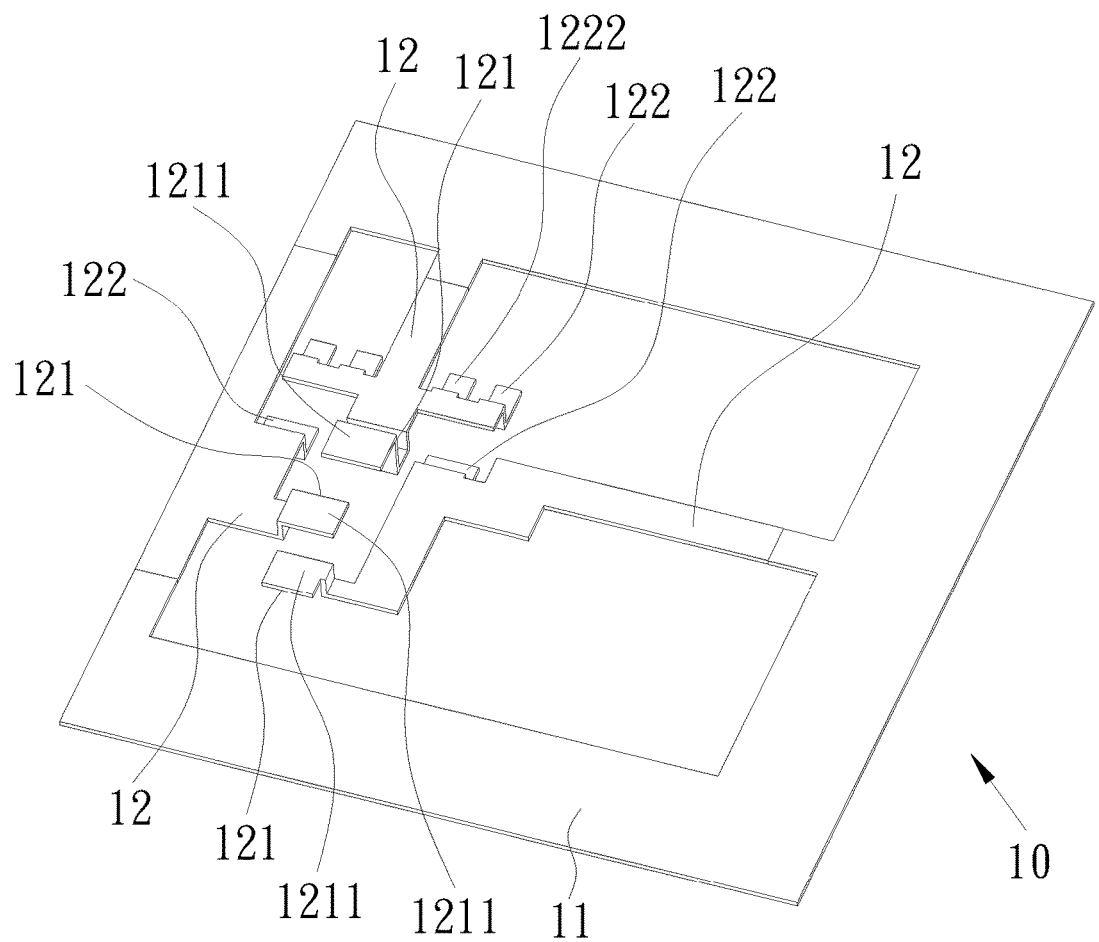
FIGS. 2-13 are embodiments of the setting method for the conductive object of the electrochemical test strip in the present invention.
Figure 3:
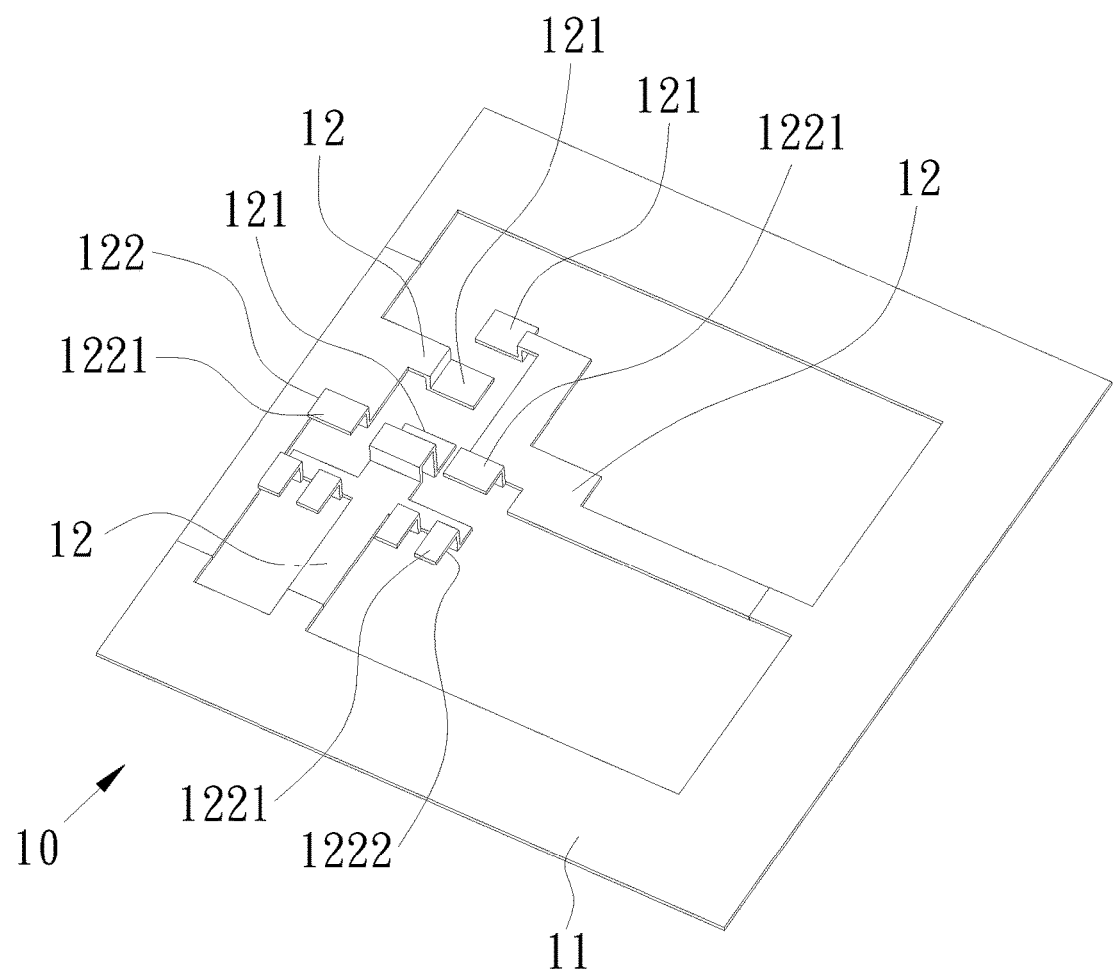

Please further refer to FIGS. 2 and 3, the aforementioned step A is to use the metal process method including punching or cropping to form a metal conductive rack 10 on a conductive metal substrate. The metal conductive rack 10 comprises a holder 11 connected to a plurality of conductive objects 12; wherein each the conductive object 12 respectively has an information reception end 121 arranged in a line correspondingly, and each the external contact surface 1211 of the information contact end 121 aligns each other. Each the conductive object 12 comprises an information outputting end 122, and a transmission contact surface 1221 included in the information outputting end 122 is disposed on an opposite side of external contact surfaces 1211, and keeps the external contact surfaces 1211 at a distance. The information outputting end 122 of the conductive object 12 has a plurality of extendable pins 1222.

The metal conductive rack 10 further serves as a surface protection layer, or a conductive protection layer can be formed on the surface of the metal conductive rack 10 after electroplating, chemical plating, and physical vapor plating (such as vapor sputtering, vapor deposition, and so on). Preferably, the conductive protection layer is nickel, gold, silver, tin, titanium, platinum, palladium, rhodium, ruthenium, iridium, chromium, iron, aluminum or is an alloy including at least two metals described above.

Figure 4:
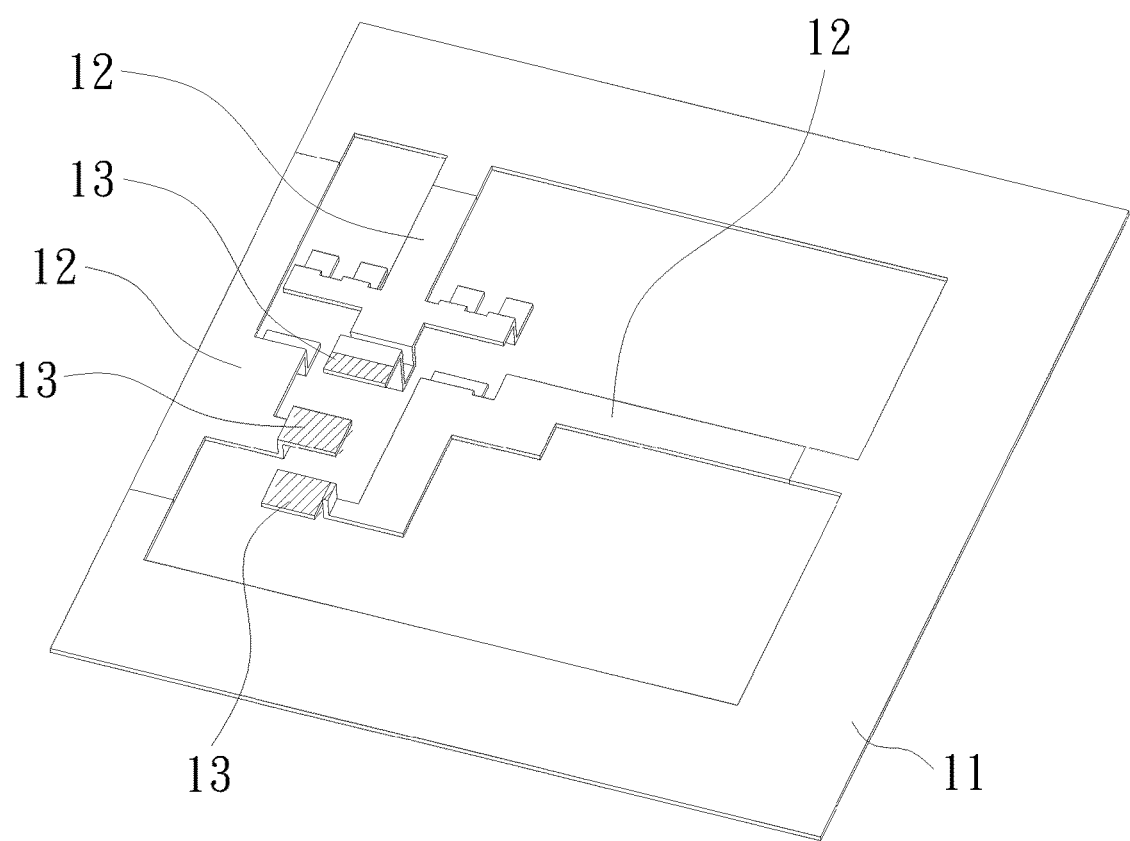
Figure 5:
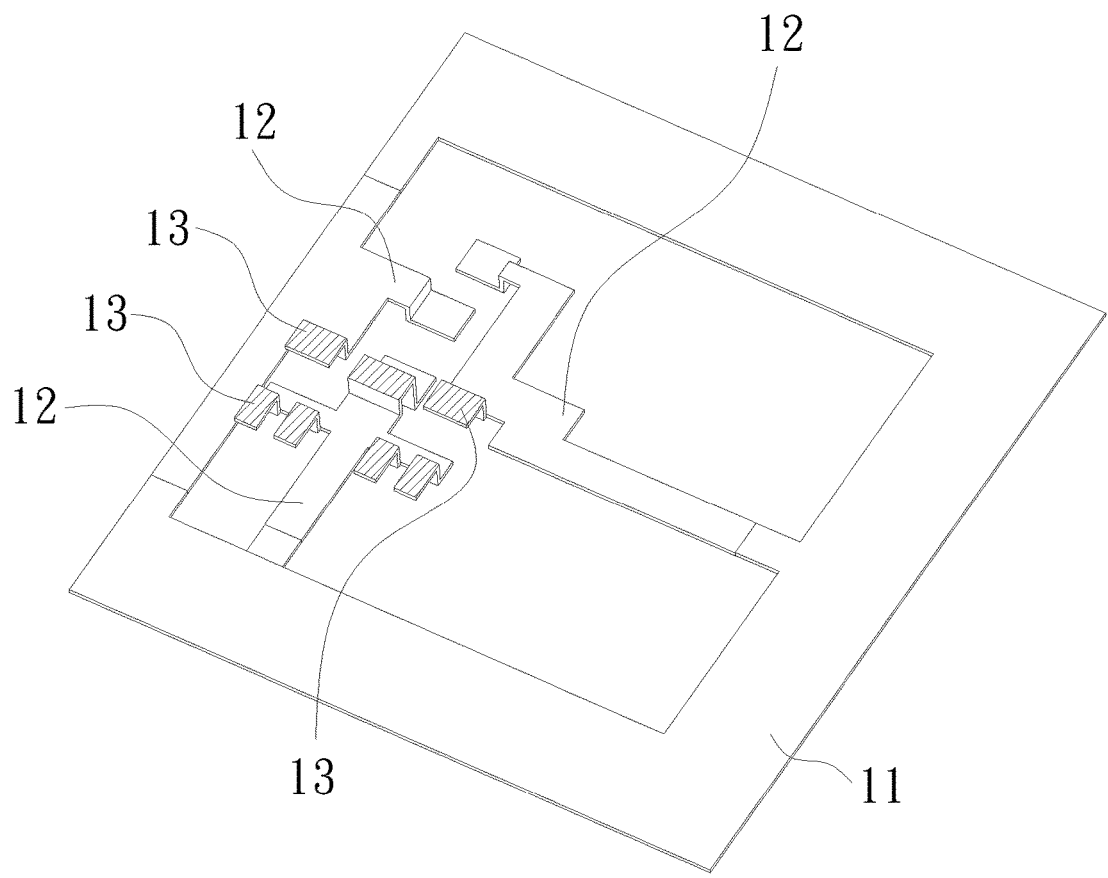

Please further refer to FIGS. 4 and 5, a strengthened signal metal layer 13 is formed on the external contact surface 1211 of the information contact end 121 and the transmission contact surface 1211 of the information outputting end 122. Preferably, the strengthened signal metal layer 13 is plated with the metal with better conduction, such as gold, silver, platinum, palladium, rhodium, ruthenium, iridium, and so on.

Figure 6:
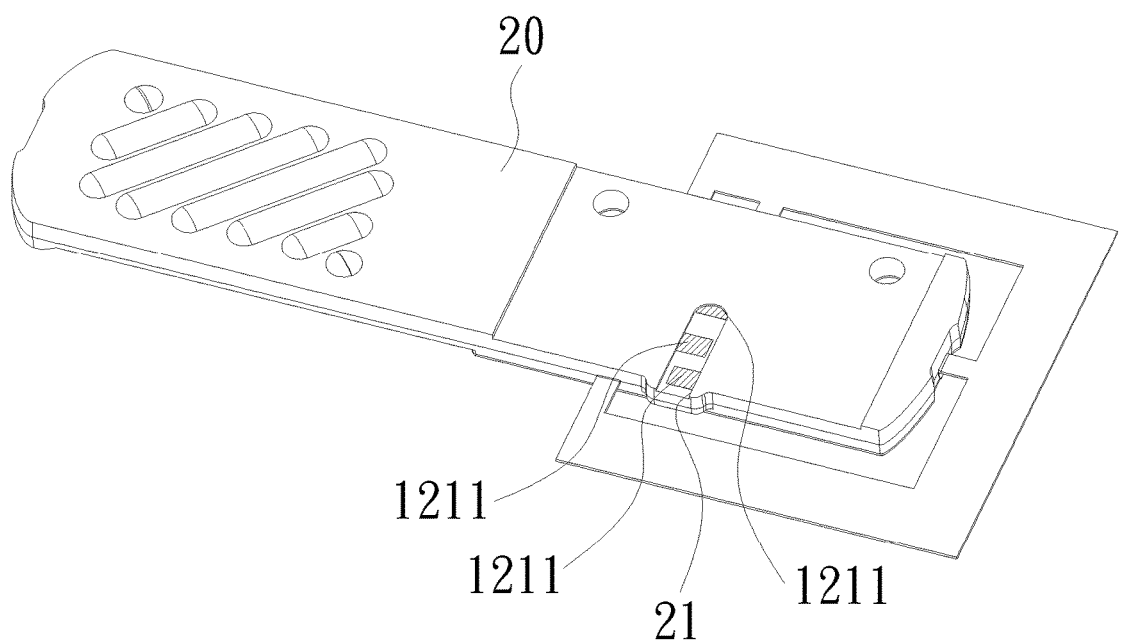
Figure 7:
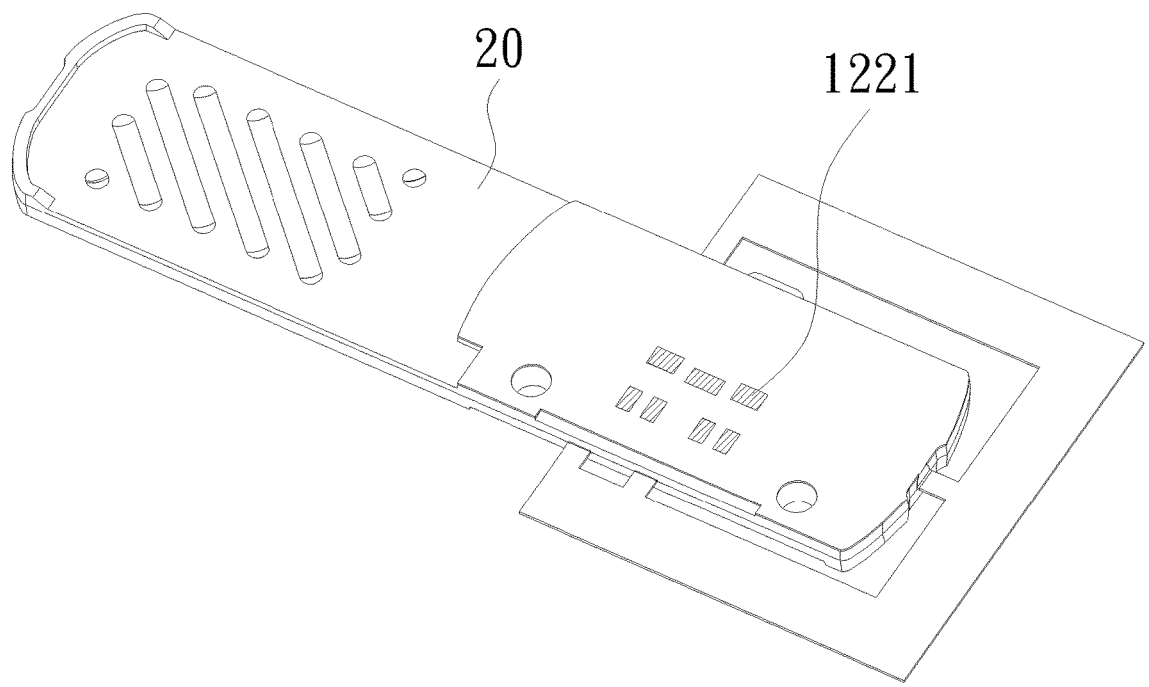

Please refer to FIGS. 6 and 7, the aforementioned step B is to inject molding the inspection body 20 of a polymer plastic material from the plurality of conductive objects 12 on the metal conductive rack 10, and the external contact surface 1211 of the information reception end 121 and the transmission contact surface 1221 of the information outputting end 122 expose from the inspection body 20.

Preferably, a side of the inspection body 20 comprises an inspection portion 21, and each the external contact surfaces 1211 of the information reception end 121 exposes from the surface of inspection portion 21. On the other hand, each the transmission contact surface 1221 of the information outputting end 122 exposes from a surface of another side of the inspection body 20.

Figure 8:
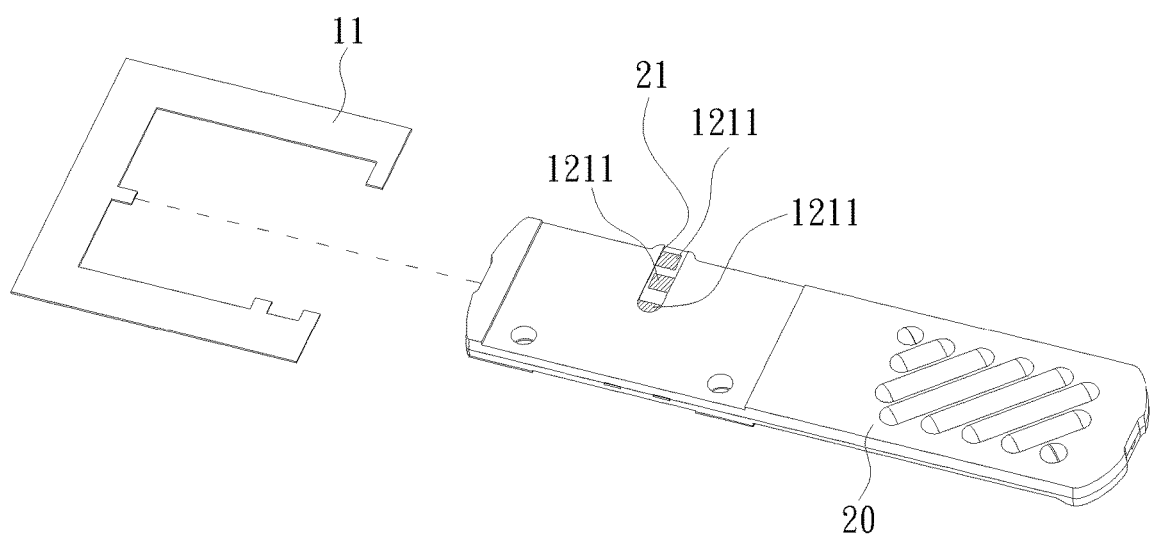

Please refer to FIG. 8, the aforementioned step C is to get the inspection body 20 from the holder 11 of the metal conductive rack 10.

Figure 9:
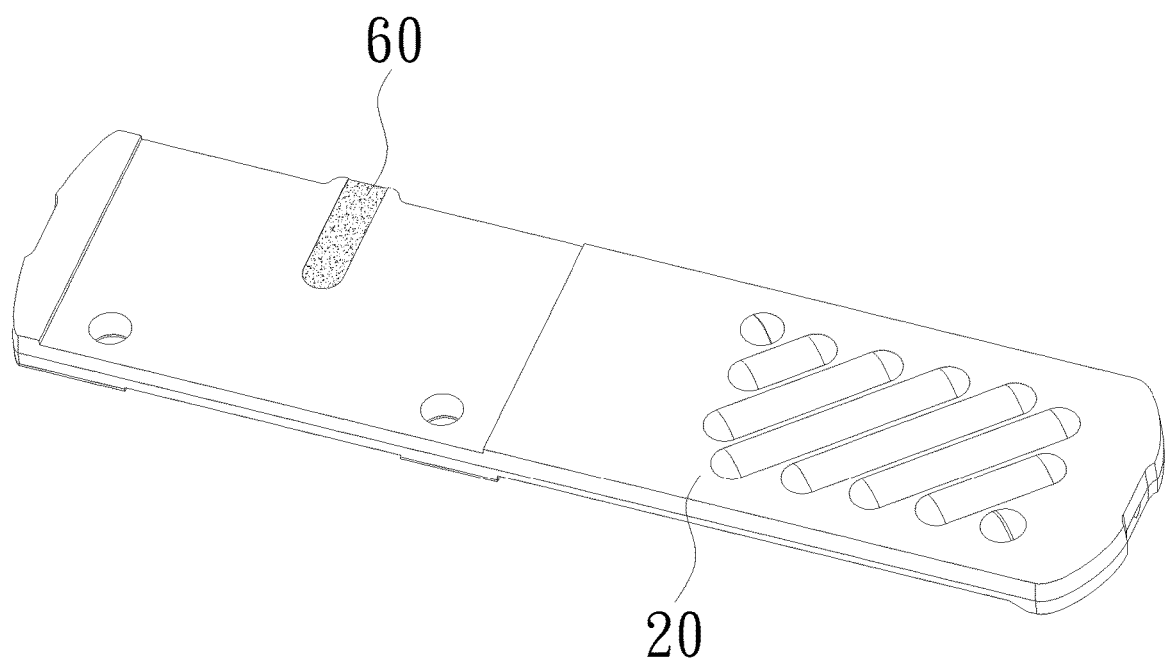
Figure 10:
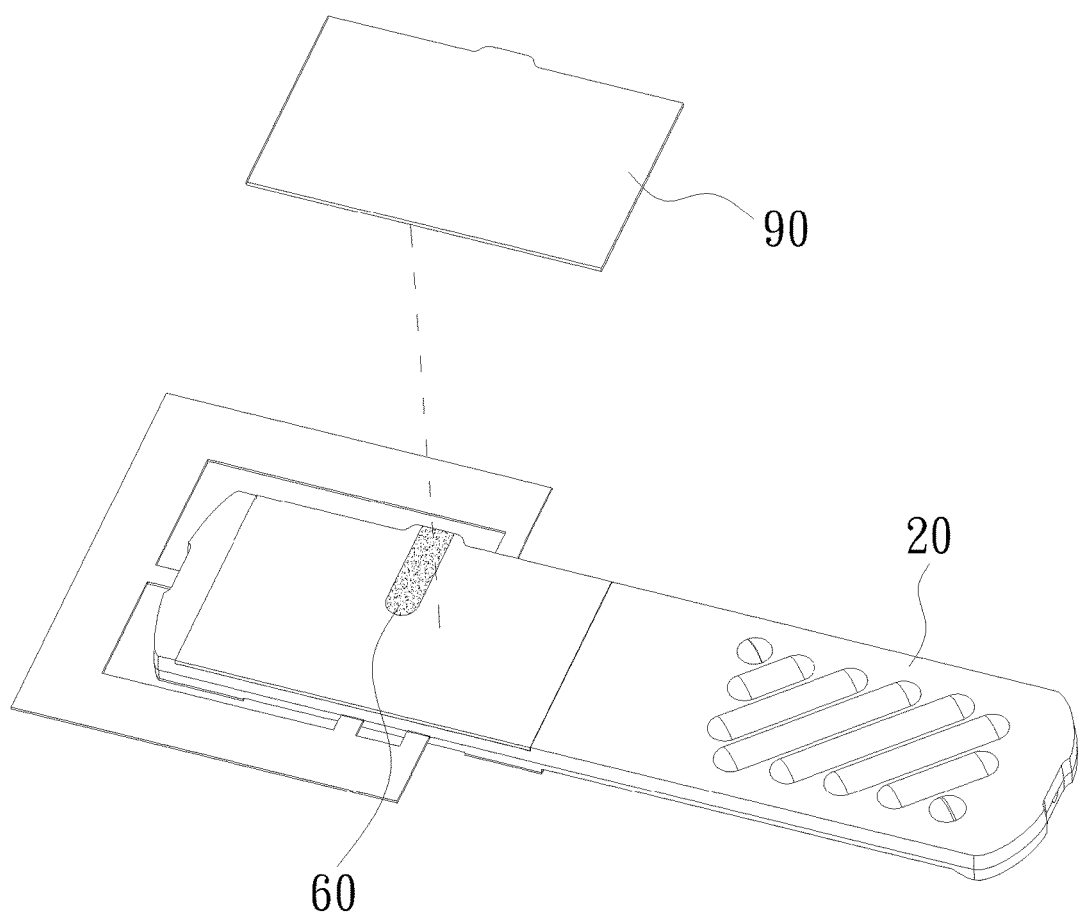

Please refer to FIGS. 9 and 10, an electrochemical reaction layer is disposed on the inspection portion 21, and an electrochemical sensing portion 60 is formed by coating, droplet or distributing chemical agents on the inspection portion 21. A cover 90 covers on the surface of the inspection body 20, and allows forming an opening on an external side of the inspection portion 21 in which liquid specimen can be dropped.

The present invention further provides another aspect of embodiment, still comprising A. molding a metal conductive rack step; B. embedded injection of a conductive inspection body step; and C. taking out the inspection body step.

Figure 11:
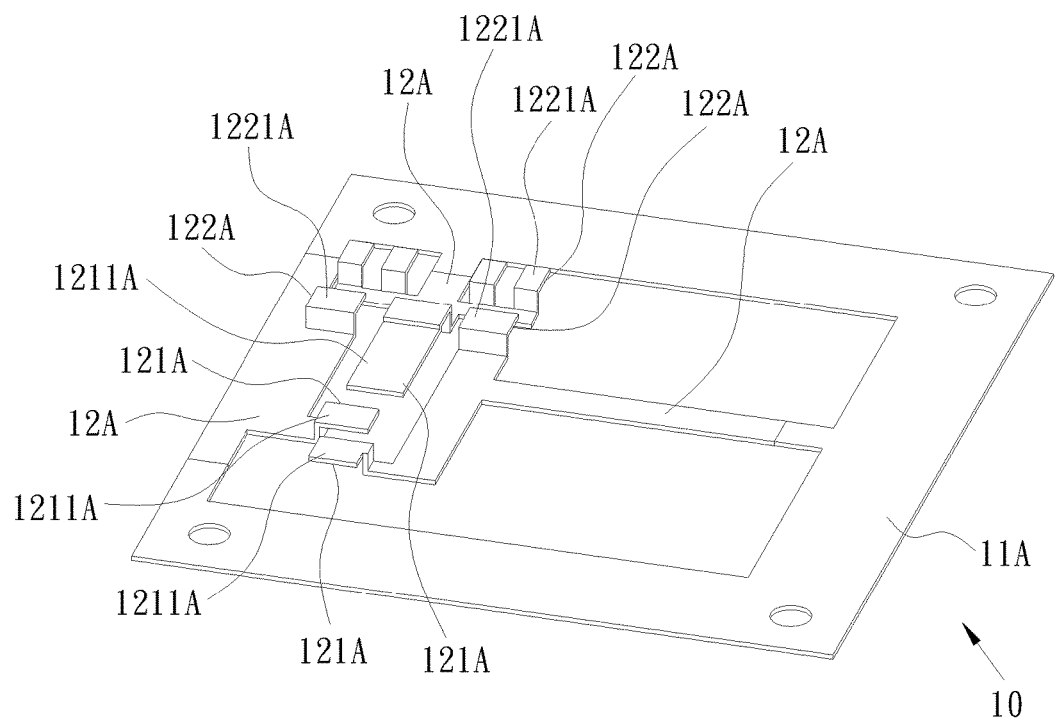

Please refer to FIG. 11, the step aforementioned A is to use the metal process method including punching or cropping to form a metal conductive rack 10A on a conductive metal substrate. The metal conductive rack 10A comprises a holder 11A connected to a plurality of conductive objects 12A; wherein each the conductive object 12A respectively has an information reception end 121A arranged in a line correspondingly, and each the external contact surface 1211A of the information contact end 121A aligns each other. Each the conductive object 12A further comprises an information outputting end 122A.

The metal conductive rack 10A further serves as a surface protection layer, or a conductive protection layer can be formed on the surface of the metal conductive rack 10A by electroplating, chemical plating, and physical vapor plating (such as vapor sputtering, vapor deposition, and so on). Preferably, the conductive protection layer is nickel, gold, silver, tin, titanium, platinum, palladium, rhodium, ruthenium, iridium, chromium, iron, aluminum or is an alloy including at least two metals described above.

Figure 12:
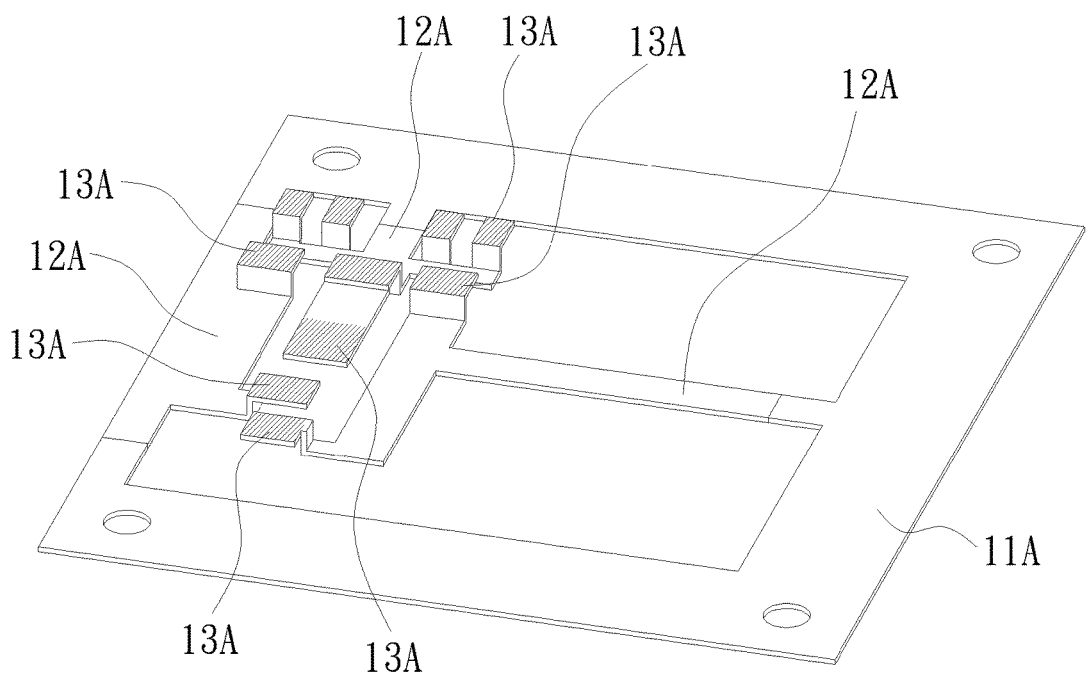

Please further refer to FIG. 12, a strengthened signal metal layer 13A is formed on the external contact surface 1211A of the information contact end 121A and the transmission contact surface 1211A of the information outputting end 122A.

Figure 13:
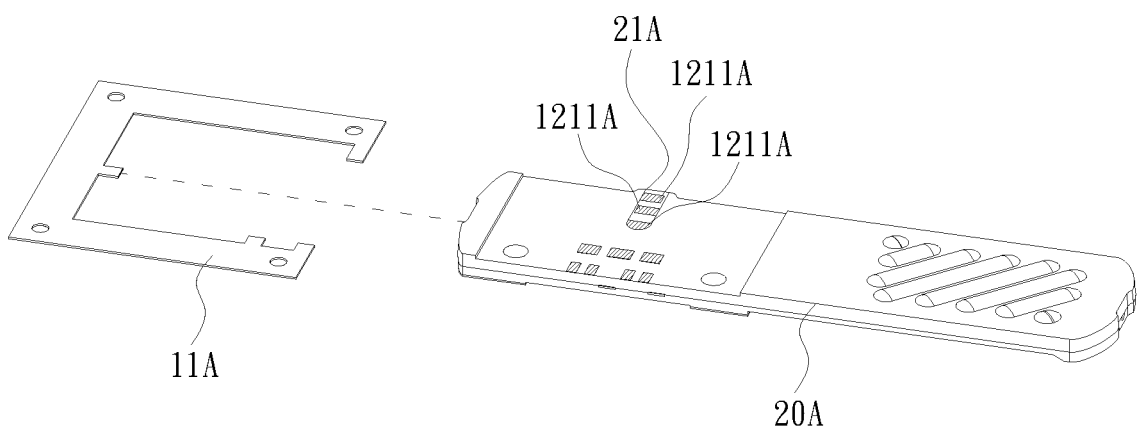

Please refer to FIG. 13, the aforementioned step B is to inject molding the inspection body 20A of a polymer plastic material from the plurality of conductive objects 12A on the metal conductive rack 10A, and the external contact surface 1211A of the information reception end 121A and the transmission contact surface 1221A of the information outputting end 122A expose from the inspection body 20A.

Preferably, a side of the inspection body 20A comprises an inspection portion 21A, and each the external contact surfaces 1211A of the information reception end 121A exposes from the surface of inspection portion 21A.

The aforementioned step C is to get the inspection body 20A from the holder 11A of the metal conductive rack 10A.

The above-mentioned descriptions represent merely the exemplary embodiment of the present invention, without any intention to limit the scope of the present invention thereto. Various equivalent changes, alternations or modifications based on the claims of present invention are all consequently viewed as being embraced by the scope of the present invention.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A setting method for a conductive object of an electrochemical test strip, comprising:
   A. molding a metal conductive rack step, to mold the metal conductive rack on a conductive metal substrate by a metal processing method, the metal conductive rack including a holder connected to a plurality of conductive objects; wherein each the conductive object comprises an information reception end having an external contact surface, and each the conductive object further comprises an information outputting end having a transmission contact surface;
   B. embedded injection of a conductive inspection body step, to inject molding the inspection body of a polymer plastic material from the plurality of conductive objects on the metal conductive rack, and the external contact surface of the information reception end and the transmission contact surface of the information outputting end exposing from the inspection body, wherein a side of the inspection body comprises an inspection portion, and each the external contact surface of the information reception end exposes from the surface of inspection portion; and
   C. taking out the inspection body step, to get the inspection body from the holder of the metal conductive rack.

2. The setting method as defined in claim 1, wherein the transmission contact surface of the information outputting end is disposed on an opposite side of the external contact surface and keeps the external contact surface at a distance, and the transmission contact surface and the external contact surface are disposed on both sides of the inspection body.

3. The setting method as defined in claim 1, wherein the transmission contact surface of the information outputting end is disposed on an identical side of the external contact side.

4. The setting method as defined in claim 1, wherein the inspection body comprises a grip portion for holding.

* * * * *